US010890343B2

(12) United States Patent
Breen (10) Patent No.: US 10,890,343 B2
(45) Date of Patent: Jan. 12, 2021

(54) SYSTEM AND METHOD FOR ASSESSMENT AND MANAGEMENT OF AIR POLLUTION EXPOSURES USING PERSONAL DEVICES

(71) Applicant: GOVERNMENT OF THE UNITED STATES AS REPRESENTED BY THE ADMINISTRATOR OF THE U.S. ENVIRONMENTAL PROTECTION AGENCY, Washington, DC (US)

(72) Inventor: Michael Scott Breen, Hillsborough, NC (US)

(73) Assignee: GOVERNMENT OF THE UNITED STATES AS REPRESENTED BY THE ADMINISTRATOR OF THE U.S. ENVIRONMENTAL PROTECTION AGENCY, Washington, DC (US)

( * ) Notice: Subject to any disclaimer, the term of this patent is extended or adjusted under 35 U.S.C. 154(b) by 2 days.

(21) Appl. No.: 16/377,744

(22) Filed: Apr. 8, 2019

(65) Prior Publication Data

US 2020/0003437 A1 Jan. 2, 2020

Related U.S. Application Data

(60) Provisional application No. 62/710,057, filed on Feb. 7, 2018.

(51) Int. Cl.
*F24F 11/00* (2018.01)
*A61B 5/11* (2006.01)
(Continued)

(52) U.S. Cl.
CPC ........ *F24F 11/0001* (2013.01); *A61B 5/0002* (2013.01); *A61B 5/0205* (2013.01);
(Continued)

(58) Field of Classification Search
CPC .... F24F 11/0001; F24F 11/56; F24F 2110/52; F24F 2110/64; A61B 5/1118;
(Continued)

(56) References Cited

U.S. PATENT DOCUMENTS

2006/0238383 A1* 10/2006 Kimchi .............. G01C 21/3667
340/995.1
2007/0273558 A1* 11/2007 Smith .................. G09B 29/007
340/995.1
(Continued)

OTHER PUBLICATIONS

Michael S. Breen, "GPS-based microenviroment tracker (MicroTrac) model to estimate time-location of individuals for air pollution exposure assessments: Model evaluation in central North Carolina", Journal of Exposure Science and Environmental Epidemiology, 2014, pp. 412-420.
(Continued)

*Primary Examiner* — Ziaul Karim
(74) *Attorney, Agent, or Firm* — Stein IP, LLC (57) ABSTRACT

A real-time system and method for personal air pollution exposure and inhaled dose management is described. A personal device (e.g., smartphone) determines personal exposure and inhaled dose metrics (e.g., daily accumulated dose), and compares daily histories of these metrics with personal health histories (e.g., self-reported daily asthma symptoms/inhaler use) to provide notifications when adverse health effects (e.g., asthma exacerbation) are likely to occur. The system notifications provide a personalized exposure/dose management tool by recommending behavioral changes to reduce exposure/dose (e.g., change time-location, time-physical activities, building operation). These behavioral changes are then used by the system to modify the real-time exposure and dose determined by the system.

17 Claims, 4 Drawing Sheets

(51) Int. Cl.
- *A61B 5/00* (2006.01)
- *A61B 5/0205* (2006.01)
- *A61B 5/0402* (2006.01)
- *F24F 11/56* (2018.01)
- *A61B 5/087* (2006.01)
- *F24F 110/52* (2018.01)
- *F24F 110/64* (2018.01)
- *A61B 5/024* (2006.01)

(52) U.S. Cl.
CPC .......... *A61B 5/0402* (2013.01); *A61B 5/1118* (2013.01); *A61B 5/486* (2013.01); *A61B 5/7275* (2013.01); *A61B 5/742* (2013.01); *A61B 5/7405* (2013.01); *A61B 5/7455* (2013.01); *F24F 11/56* (2018.01); *A61B 5/024* (2013.01); *A61B 5/087* (2013.01); *A61B 2560/0242* (2013.01); *A61B 2562/0219* (2013.01); *F24F 2110/52* (2018.01); *F24F 2110/64* (2018.01)

(58) Field of Classification Search
CPC ....... A61B 5/742; A61B 5/486; A61B 5/7405; A61B 5/7455; A61B 5/0002; A61B 5/0205; A61B 5/0402; A61B 5/7275; A61B 5/087; A61B 2562/0219; A61B 2560/0242; A61B 5/024; A61B 5/0022; A61B 5/08; A61B 5/4845; A61B 5/1112; A61B 2505/07; A61B 2503/12; A61B 5/7264; G16H 20/30; G16H 20/70

See application file for complete search history.

(56) References Cited

U.S. PATENT DOCUMENTS

| | | | |
|---|---|---|---|
| 2015/0335834 A1* | 11/2015 | Anandhakrishnan | A61M 15/009 128/203.12 |
| 2016/0270718 A1* | 9/2016 | Heneghan | G16H 50/30 |
| 2018/0004211 A1* | 1/2018 | Grimm | G05D 1/0214 |
| 2018/0087922 A1* | 3/2018 | Wu | G09B 29/007 |
| 2018/0325422 A1* | 11/2018 | Sokol | A61B 5/7275 |

OTHER PUBLICATIONS

Michael S. Breen, "Air Pollution Exposure Model for Individuals (EMI) in Health Studies: Evaluation for Ambient PM2.5 in Central North Carolina", Environmental Science & Technology, 2015, pp. 14184-14194.

* cited by examiner

SYSTEM AND METHOD FOR ASSESSMENT AND MANAGEMENT OF AIR POLLUTION EXPOSURES USING PERSONAL DEVICES

CROSS-REFERENCE TO RELATED APPLICATIONS

This application claims the benefit of priority to U.S. Application No. 62/710,057, filed Feb. 7, 2018, in the United States Patent and Trademark Office. All disclosures of the document named above is incorporated herein by reference.

BACKGROUND OF THE INVENTION

1. Field of the Invention

Aspects of the present invention relate to a system and method and application to assess and manage air pollution exposure of a user in which a personal device (e.g., a mobile device such as a smart phone).

2. Description of the Related Art

To better understand people's contact with air pollutants and their potential for adverse health effects, it is useful to estimate how much time they spend in different locations and what the air pollutant concentrations are in those locations. Using currently available personal portable air monitors to collect this information has several limitations, including burden on participants, cost, and need for substantial technical expertise.

Alternatively, the currently available exposure models must be used by specially-trained researchers, and near real-time predictions are not possible since large and diverse input data (e.g., high temporally resolved air pollution concentrations, weather, time-locations) must be collected, organized, and processed by complex exposure models.

The Environmental Protection Agency (EPA) AirNow website (https://www.airnow.gov/) and smartphone application (AIRNow) provides current outdoor air pollution conditions based on local outdoor monitors and outdoor air quality models. However, outdoor monitors or models cannot determine personal exposures (=concentration (mass/volume of air) of air pollutant at person's location) since they do not account for attenuation of outdoor air pollutants when a person is indoors, where the person spends most of his/her time.

Wearable air pollution exposure sensors have several limitations, including cost, they are burdensome to wear, cannot be covered by clothing, require substantial technical expertise to operate, have low accuracy due to low cost technology used (*Nature*, Vol 535, Jul. 7, 2016 p. 29-31), etc.; http://www. nature.com/polopoly_fs/1.20195!/menu/main/topColumns/topLeftColumn/pdf/535029 a.pdf).

SUMMARY OF THE INVENTION

Aspects of the present invention account for time-specific and building-specific attenuation of outdoor air pollutants, and the time people spend outdoors and within various indoor locations (e.g., home, work, school, inside vehicles).

Aspects of the present invention determine personal air pollution exposure with only a smartphone, which are used daily by a large percentage of the general population, and uses high accuracy input data from local outdoor air pollution monitors. Also, this invention determines air pollution exposure (i.e., concentration at breathing zone) and inhaled dose (i.e., mass within respiratory tract).

Additional aspects and/or advantages of the invention will be set forth in part in the description which follows and, in part, will be obvious from the description, or may be learned by practice of the invention.

To address cost and technical limitations, a personal device (such as, for example, a smart phone and sometimes referred to as "smart phone,") mobile application that predicts near real-time air pollution exposures has been developed. A mobile application (currently named TracMyAir, and developed by the EPA), may be downloadable from a source such as a mobile application store. The mobile application (hereinafter also referred to as "the application" or "the app") uses input data available from the personal device, which includes:

- near real-time outdoor air pollution measurements from local monitors (e.g., EPA's AirNow Application Programming Interface);
- current local weather (e.g., temperature, wind speed);
- user's current location; and
- user's home characteristics (e.g., floor area, year built, number of stories);
- user's current home operating conditions (e.g., window fan settings, open window status, indoor temperature settings, air cleaner settings);
- user's current physical activity level or respiratory ventilation rate;
- user's demographics (e.g., age, gender, weight, height);
- satellite-based images of earth and building footprints;
- user's street address for home, work, school; and
- user's current health status.

It is also conceivable that the personal device is a device that is somewhat less mobile than smartphone, and may include such devices as a laptop, desktop, or other computing device, which is still able to monitor the location and physical activity of a user.

The application will run various models that account for time spent in different microenvironments—such as indoors and outdoors, at home, work, and in vehicles—and the potentially lower amount of outdoor air pollution present indoors, which depends on daily weather conditions, building characteristics, building operating conditions, and type of air pollutant (e.g., ozone, particulate matter).

Using smart phones to automatically collect the large and diverse input data, integrate the data with exposure models, and predict near real-time air pollution exposures, will be a more efficient and cost-effective method for researchers to apply air pollution exposure predictions for health studies. Automated predictions from the application can also broaden the range of health studies feasible, which are often limited by availability of personal exposures.

Using smart phones eliminates the cost and burden of carrying separate GPS data logger devices.

Using smart phones allows for integration (e.g., via Bluetooth communication) with wearable health monitors to determine personal health effect responses to air pollution exposures.

Using smart phones allows for integration (e.g., via Bluetooth communication) with wearable physical activity sensors (e.g., accelerometers, wearable respiratory ventilation sensors) to predict inhaled dose.

Near real-time predictions and personalized smart phone notifications will inform people when they could/should modify their behavior (e.g., go indoors, close windows, and re-schedule outdoor exercise) to help reduce air pollution exposures.

Using outdoor air pollution forecasting models will better inform people as to how to reduce exposures.

This research can improve exposure assessments for health studies that provide the scientific basis for air pollution regulations, and for developing public health strategies to help susceptible people, like those with asthma, reduce their exposure to air pollution.'

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Reference will now be made in detail to the present embodiments of the present invention, examples of which are illustrated in the accompanying drawings, wherein like reference numerals refer to the like elements throughout. The embodiments are described below in order to explain the present invention by referring to the figures. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Figure 1:
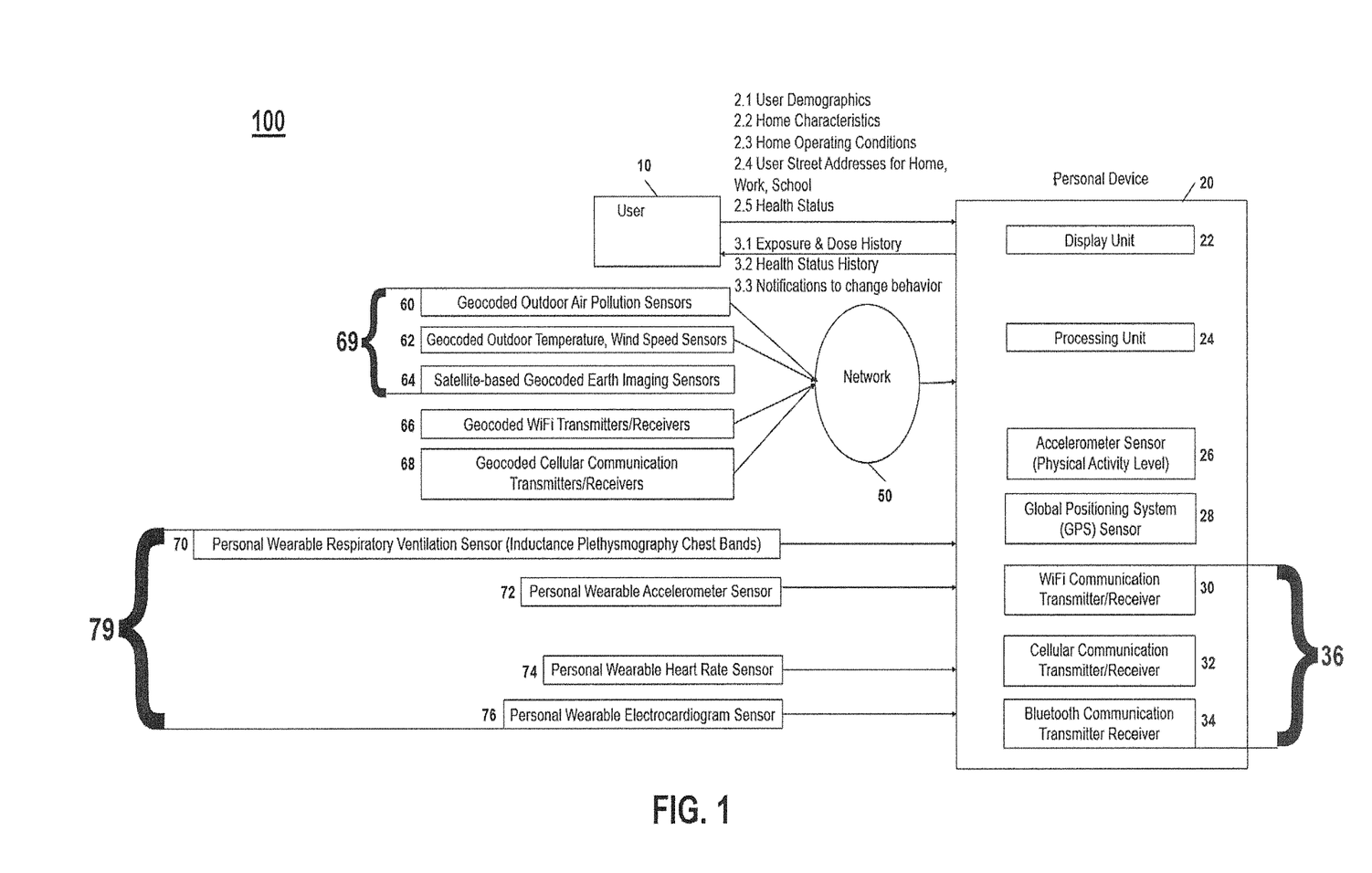
FIG. 1 is a diagram of an entire system for assessing and managing air pollution exposures according to an embodiment of the present invention.

FIG. 1 is a diagram of an entire system 100 for assessing and managing air pollution exposures using a personal device 20, such as, only by way of example, a mobile phone (also referred to as a smartphone) or smartwatch, according to an embodiment of the present invention. It is also conceivable that the personal device 20 is a device that is somewhat less mobile than a smartphone or smartwatch, and may include such devices as a laptop, desktop, or other computing device, which is still able to monitor the location and physical activity of a user. It is also contemplated that in the future, other portable device technologies will be developed.

A user 10, a person on which assessment and management of air pollution is to be performed, will generally carry around or have nearby a personal device (a mobile device, such as a smartphone or smartwatch by way of example, but not limited thereto) 20. The personal device 20 has at least a display unit 22, a processing unit 24, an accelerometer sensor 26, a global positioning system 28, a WiFi communication transmitter/receiver 30, a cellular communication transmitter/receiver 32, and a Bluetooth communication transmitter/receiver 34.

The processing unit 24 controls the other elements of the personal device 20. The processing unit may be implemented in various kinds of hardware (including, but not limited to, chips, CPUs, GPUs, FPGAs, ASICs, DSP, APU, and any other capable processing component) that are all treated as "processing elements" for the purposes of this disclosure. These processing elements may be singular or plural. The processing element may use volatile or non-volatile storage or memory including but not limited to ROM, RAM, SDRAM, DRAM, SRAM, flash Memory, MRAM, D-RAM or P-RAM. The processing unit 24 contains software code, or a non-transitory machine readable medium comprising instructions that, when executed performs operations to receive inputs and generate outputs to the other elements of the personal device 20. The accelerometer sensor 26 detects the level of activity of the user 10 when the user is wearing the personal device 20, the GPS sensor 28 continuously determines the specific location of the user 10, and communication with elements outside of the personal device 20 can be handled through by WiFi, cellular or Bluetooth, using the WiFi communication transmitter/receiver 30, the cellular communication transmitter/receiver 32 and the Bluetooth communication transmitter/receiver 34, which can collectively be called a transmitter/receiver 36.

The personal device 20 communicates with a network 50 via the transmitter/receiver 36 (either the WiFi communication transmitter/receiver 30, the cellular communication transmitter/receiver 32 or the Bluetooth communication transmitter/receiver 34, or any combination thereof.

Geocoded outdoor air pollution sensors 60, geocoded outdoor temperature/wind speed sensors 62, satellite-based geocoded earth imaging sensors 64, geocoded WiFi transmitter/receivers 66 and geocoded cellular communication transmitters/receivers 68 can provide different types of weather and air pollution data (throughout the specification, the terms "data" and "information" can be used interchangeably) to the network 50, which can then be received by the personal device 20 via the transmitter/receiver 36 (any of the WiFi communication transmitter/receiver 30, cellular communication transmitter/receiver 32 and the Bluetooth communication transmitter/receiver). Any combination of the aforesaid, including subsets thereof, and other types of information related to the environment near the user 10 may be provided in addition to or instead of the aforementioned environmental inputs.

The outdoor air pollution sensors 60 provide high temporal resolution (e.g., hourly) concentrations of various air pollutants (e.g., particulate matter, ozone), which are used as inputs for an exposure model. The outdoor temperature and wind speed sensors 62 detect outdoor temperature which are used as inputs for a home infiltration model. The satellite-based geocoded earth imaging sensors 64 provide images of building footprints, which are used as inputs for a time-microenvironment model to determine when a person is indoors or outdoors at home, work, or school. These sensors 60, 62 and 64 are located outdoors to provide outdoor information (environmental data) which are deemed relevant for assessing air pollution exposure of the user 10 whether the user 10 is indoors or outdoors. The geocoded WiFi transmitter/receivers 66 and geocoded cellular communication transmitters/receivers 68 send the environmental data to the network 50.

The geocoded outdoor air pollution sensors 60, geocoded outdoor temperature/wind speed sensors 62, satellite-based geocoded earth imaging sensors 64, may be collectively referred to as environmental data sensors 69. The geocoded WiFi transmitter/receivers 66 and geocoded cellular communication transmitters/receivers 68 may be collectively referred to as environmental data sensors 69 to produce the environmental data.

Through graphical user (GUI) interfaces of the application which are presented on the display unit 22, the user 10 can input information (such as by touch) on him/herself (hereinafter the term he/him will be used for ease of use), such as the user demographics (such as age, gender, weight, height, etc., from the user) 2.1, characteristics of the home of the user (such as floor area, year built, number of floors) 2.2, operating conditions of the home (such as window fan settings, open window status, indoor temperature/thermostat settings, air cleaner settings) 2.3, the user's home, work and school street addresses 2.4, and the health status of the user 2.5 (collectively called personal information). The home characteristics 2.2 and the home operating conditions 2.3 are examples of home condition data. Other types of information related to the user 10 or the typical environments of the user 10 may be provided to the personal device 20 in addition or instead of the aforementioned user provided inputs. Some of this information may be provided to the personal device 20 using automated systems (such as WiFi-enabled home thermostats, or air cleaners).

Aside from what the user 10 personally provides to the personal device 20, the user may have a personal wearable respiratory ventilation sensor 70 (which may comprise plethysmography chest bands), a personable wearable accelerometer sensor 72, a personal wearable heart rate sensor 74 and/or a personal wearable electrocardiogram sensor 76, these sensors being collectively referred to as personal wearable sensors or personal condition sensors 79. Other types of wearable or detection sensors/devices related to various conditions of the user 10 or the typical environments may be provided to the personal device 20 in addition or instead of the aforementioned user wearable input sensors. The wearable respiratory ventilation sensor 70 measures inhaled air ventilation (volume of air per minute), which is used to calculate inhaled dose. The wearable accelerometer sensor 72 measures the user's physical activity level, which is also used to determine inhaled air ventilation. The respiratory ventilation sensor 70 output data to be used for two different methods to determine inhaled air ventilation. The wearable heart rate sensor 74 measures heart beats per minute, and the personal wearable electrocardiogram sensor 76 measures electrical activity of the heart, which are both used to determine health effects of air pollution. For an example of these sensor devices with these wearable sensor technologies, see Hexoskin biometric shirt (https://www.hexoskin.com/).

The personal device 20 will receive the user provided inputs (personal information) 2.1-2.5, the user condition inputs from the wearable sensors 70, 72, 74 and 76, the weather and pollution (environmental) inputs from the environmental data sensors and transmitters/receivers 60, 62, 64, 66 and 68, GPS information from the GPS sensor 28, a physical activity level information from the accelerometer sensor 26, and all (or any combination) of these inputs, or other inputs, will be provided to the processing unit 24. The processing unit 24 will use all (or any combination of these inputs) to assess the air pollution to which the user 10 is being exposed and how the user 10 is intaking the air pollution and determine what actions, if any, the user should take as a result of the assessment. Consequently, the processing unit 24 displays on the display unit 22 exposure and dose history 3.1, health status history 3.2 and notifications to change behavior on the display unit 22 of the personal device 20 to inform the user 10 of these types of information. The notifications may also be in the form of vibration or sound emanating from the personal device 20.

The GPS sensor 28 is able to determine an exact location of the personal device 20 at any given moment. Thus, the GPS sensor 28 can determine whether the user 10 is inside a building or outside. The exact location of the personal device 20 may also be determined by geocoded WiFi (is through the WiFi communication transmitter/receiver) or geocoded cellular towers (is this through the cellular communication transmitter/receiver). Each such element may be considered a locator. In one aspect, a certain degree of pollution attenuation is used for all types of buildings. However, it is understood that different types of buildings (for example, houses, office buildings, schools) have different degrees of pollution attenuation. With the user 10 entering into the application the user's street addresses for home, work and school 2.4, the GPS sensor 28 will know the type of building the user is in at that moment, and a pollution attenuation factor can be provided to that type of building for the user 10. It is contemplated that the application will be able to become even more accurate, in assessing the specific building or car the user is in to assess air pollution exposure of the user 10.

Figure 2:
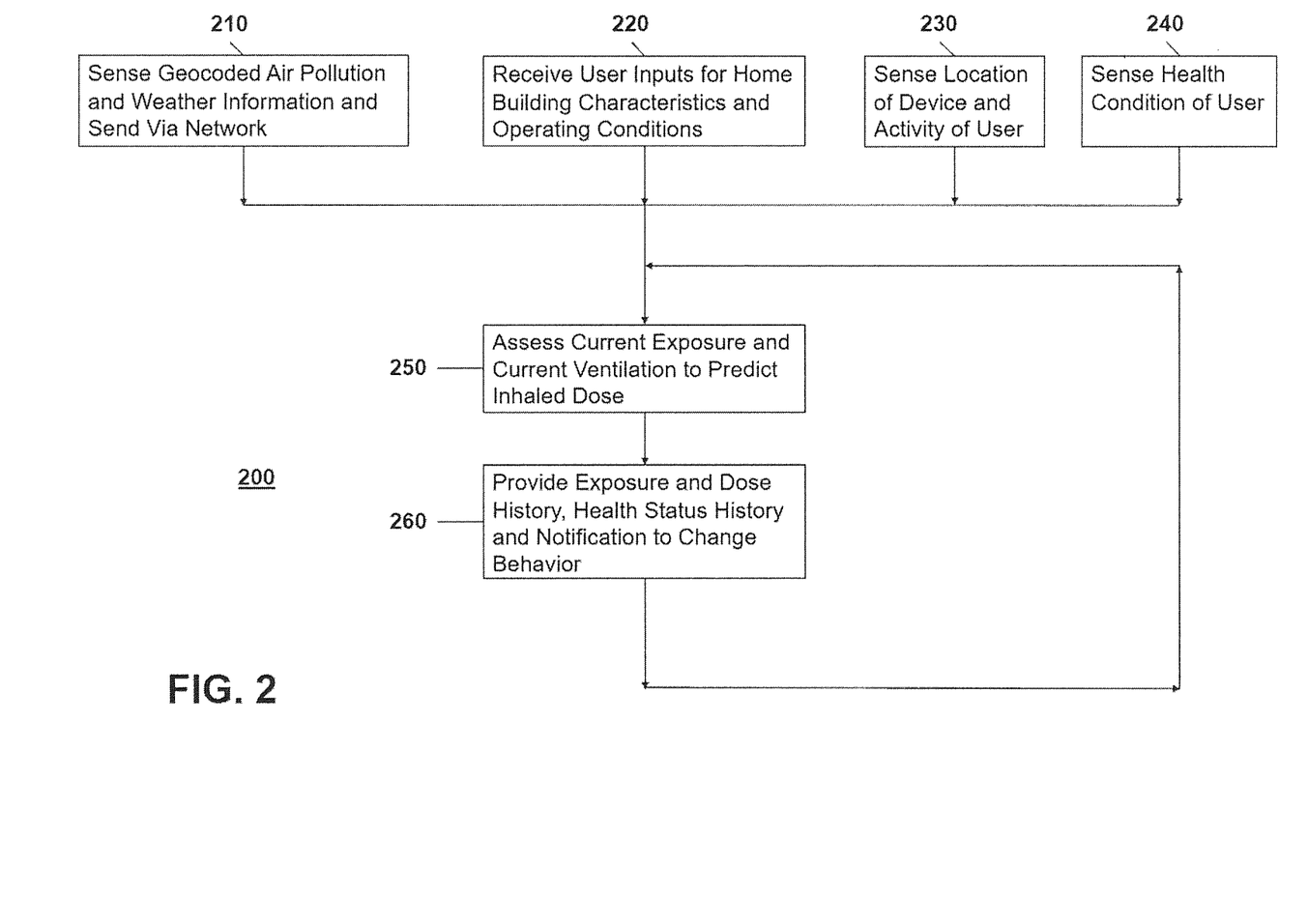
FIG. 2 is a flow diagram of a process for continuously assessing and managing air pollution exposures in near real-time using the mobile device 20 according to an embodiment of the present invention.

FIG. 2 is a flow diagram of a process for continuously assessing and managing air pollution exposures in near real-time using the personal device 20.

In operation 210, the geocoded outdoor air pollution sensors 60, geocoded outdoor temperature/wind speed sensors 62, satellite-based geocoded earth imaging sensors 64, geocoded WiFi transmitter/receivers 66 and geocoded cellular communication transmitters/receivers 68 sense and then send different types of weather, air pollution, and satellite imagery data to the network 50, which can then be received by the personal device 20.

In operation 220, the user 10 can input the personal information on himself such as the user demographics 2.1, the home characteristics 2.2, the home operating conditions 2.3, user street addresses for home, work, and school 2.4 to the personal device 20, and health status information 2.5.

In operation 230, the GPS sensor 28 and the accelerometer sensor 26 determine the location and the motion of the personal device 20 automatically when the application is in use.

In operation 240, the health condition data of the user 10 is monitored through the personal condition sensors 79 (the wearable respiratory ventilation sensor 70 (which may comprise plethysmography chest bands), the personable wearable accelerometer sensor 72, the personal wearable heart rate sensor 74 and the personal wearable electrocardiogram sensor 76), or user provided health condition data 2.5

The sensed geocoded air pollution and weather information, the user inputs for user demographics, home characteristics, operating conditions, and building addresses, the sensed location of the personal device 20 and activity (physical level) of the user 10, and the sensed health conditions of the user 10 are provided to the processing unit 24 of the personal device 20.

In operation 250, the processing unit 24 assesses the current exposure and current ventilation of the user 10 to predict the inhaled dose of air pollution for the user 10. The process continues for operations 210, 220, 230 and 240 so as to maintain real-time data on the air pollution exposure and user ventilation, to continuously predict the inhaled dose of air pollution for the user 10.

In operation 260, the processing unit 24 determines the air pollution exposure and dose history 3.1, and health status history 3.2 of the user 10, and initiates the display unit 22 to produce a notification 3.3 to the user 10 to modify his behavior based upon the predicted inhaled dose and the current user activity. The display unit 22 can also display the exposure and dose history 3.1, as well as the health status history 3.2 of the user 10. The exposure and dose history 3.1 and the health status history 3.2 can then be fed back with new inputs 210, 220, 230 and 240 to update the exposure and dose history 3.1 and health status history 3.2, and determine whether the notification should be altered in any way.

Figure 3:
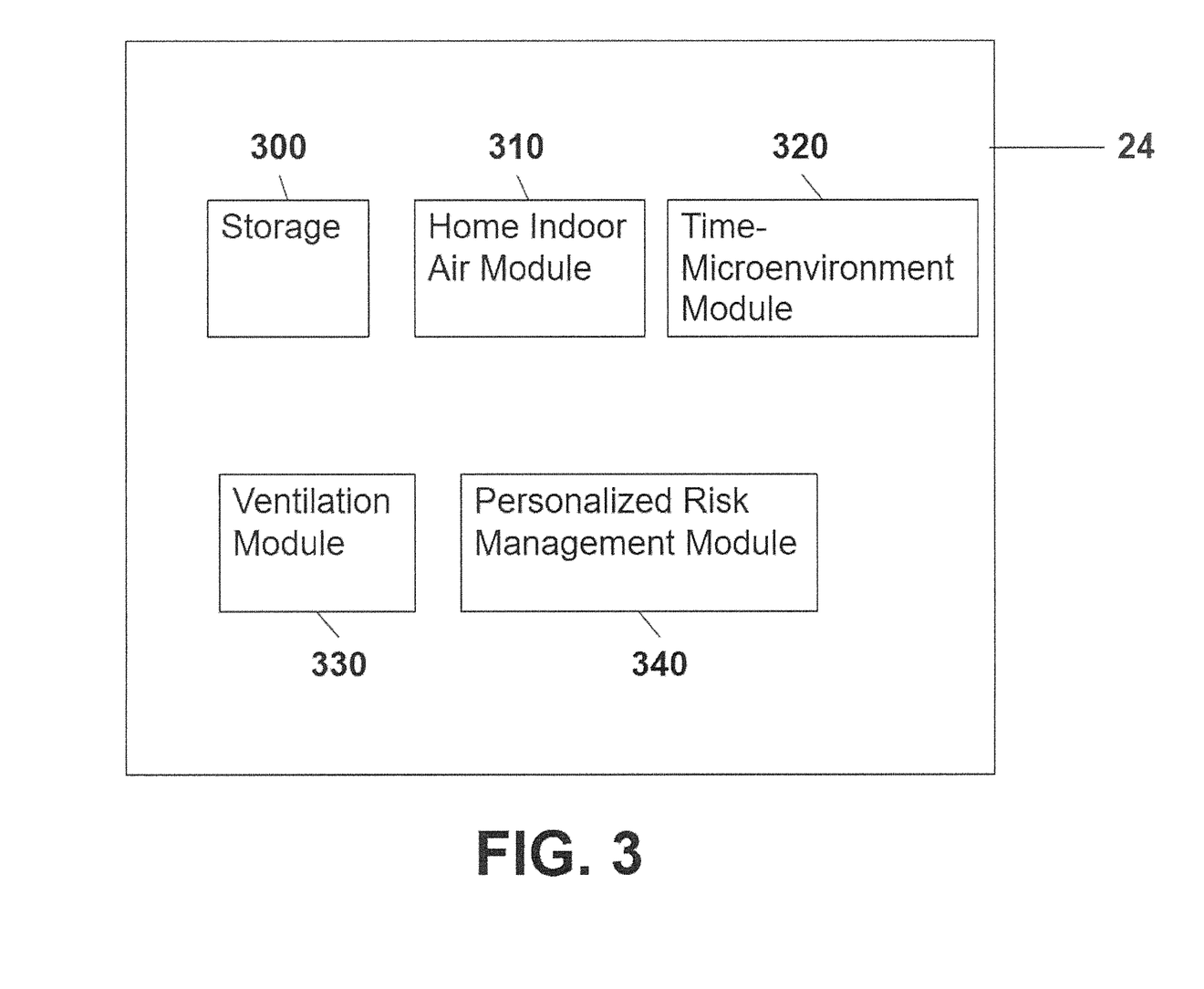
FIG. 3 is a block diagram of the processing unit according to an embodiment of the present invention.

FIG. 3 is a block diagram of the processing unit 24 shown in FIG. 1. The processing unit 24 comprises a storage 300, an indoor air quality module 310, a time-microenvironment module 320, a ventilation module 330, and a personalized risk management module 340 in the storage 300 stores: the exposure history, the inhaled dose history, the health status history, the personal information provided by the user 10: demographics 2.1, home characteristics 2.2, the home operating conditions 2.3, the street address for home, work, school 2.4, and the health status 2.5.

Figure 4:
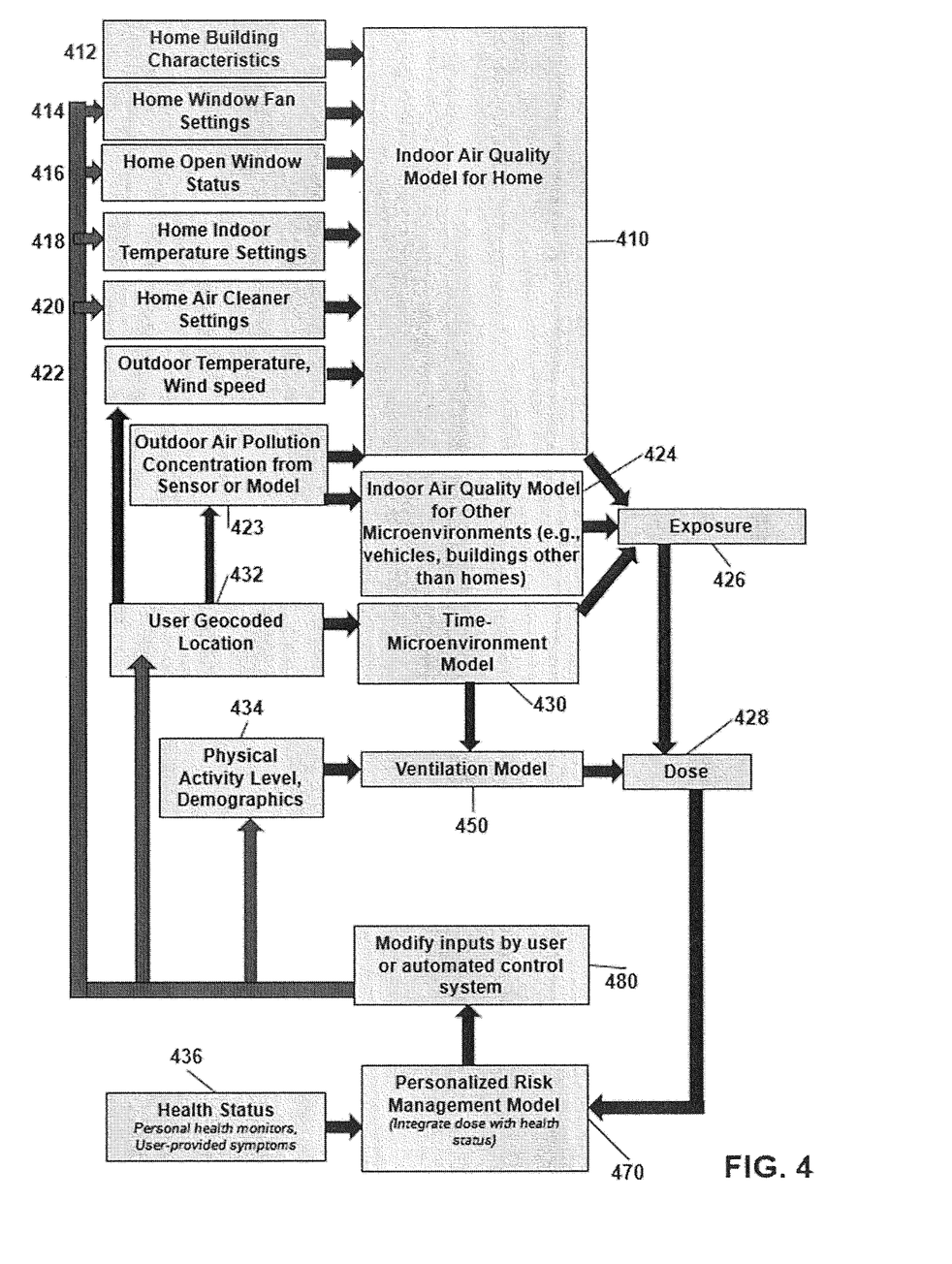
FIG. 4 shows a conceptual model of the app shows with its various inputs, models, and outputs/predictions according to an embodiment of the present invention.

FIG. 4 shows a conceptual model of the application with its various inputs, models, and outputs/predictions. The app predicts in real-time personal exposures (i.e., concentrations at the breathing zone) and inhaled doses (amount in respiratory tract) for multiple types of outdoor-generated air pollutants (i.e., airborne particles and gases). Model predictions are displayed on the display unit 22 of the personal device 20, and recommendations are provided by the application to help the user 10 take action and make informed decisions to reduce his air pollution exposure and inhaled dose. These actions could include reducing physical activity level, changing his location (e.g., going indoors), changing home building characteristics and operating conditions (e.g., closing windows, operating home air filtration systems). Personal health conditions (via user-provided symptoms (health status 2.5) and/or health monitors (the personal condition sensors 79) are integrated with the predicted exposure and dose in a risk management model to provide in real-time recommended actions to minimize adverse health effects due to air pollution exposure and dose by modifying behavior.

Model Overview

The application includes multiple models to predict exposure and inhaled dose from outdoor-generated air pollution. A building air exchange rate is linked to a mass-balance infiltration model to predict indoor air pollution concentrations for homes. The residential air exchange rate model determines the air pressure difference across a building envelope based on the indoor-outdoor temperature difference and wind speed 418, 422, 423. The air exchange rate model accounts for uncontrollable air leakage based on the home building characteristics 412, controllable air leakage from open windows 416, and mechanical ventilation from window fans 414. Building-specific infiltration factors are used to predict current indoor air pollution concentrations for other microenvironments (e.g., work, in-vehicle, other indoor locations). A time-microenvironment model is used to determine a person's current location, which is called a microenvironment (i.e., outdoors, indoors at home, work, school, in-vehicle, other buildings) from a smartphone's GPS data. A ventilation model is used to predict a person's current respiratory ventilation rate from a smartphone's accelerometer data. To predict a person's exposure, the current outdoor air pollution concentration (data from local air monitoring station connected to the internet) is multiplied by the appropriate infiltration factor for the current microenvironment. To predict a person's inhaled dose, the current exposure is multiplied by the current ventilation rate.

Indoor Air Quality Model for Homes

The indoor air quality model for homes is performed by the indoor air quality module 310 of the processing unit 24. The indoor air quality model, by way of example:

(1) Uses a mass-balance infiltration model as described in Breen et al. 2015, *Air Pollution Exposure Model for Individuals (EMI) in Health Studies: Evaluation for Ambient $PM_{2.5}$ in Central North Carolina, Environmental Science & Technology*, 2015, pages 14184-14194 for outdoor-generated air pollutants.

(2) Accounts for indoor removal of air pollutants from operating home air cleaners, and operating heating, ventilation, and air conditioning (HVAC) systems based on filter characteristics and airflow across filters.

(3) In FIG. 4, the types of home building characteristics 412 of the user 10, home window fan settings 414, home open window settings 416, home indoor temperature settings 418, home hair cleaner settings 420, outdoor temperature/wind speed 422, and outdoor air pollution concentration from sensor or model 423 are used by the home indoor air quality module 310 to generate indoor air pollutant concentrations.

(4) The outdoor air pollution concentration 423 is an input for the indoor air quality model for home 410 and for an indoor air quality model for other microenvironments 424, such as air pollutant concentrations for vehicles and buildings other than a home.

Alternatively, by way of example, an indoor air quality model for homes completely different, which does not use mass balance model, may be used.

(5) using, by way of example, infiltration factors to determine indoor concentrations for vehicles and buildings other than homes as described in Breen et al. 2015, 2015, *Air Pollution Exposure Model for Individuals (EMI) in Health Studies: Evaluation for Ambient $PM_{2.5}$ in Central North Carolina, Environmental Science & Technology*, 2015, pages 14184-14194.

Alternatively, by way of example, an indoor air quality model for other microenvironments, which does not include infiltration factors, may be used.

(6) Accounts for indoor removal of air pollutants from vehicle-specific re-circulation systems with cabin filters, and from building-specific heating, ventilation, and air conditioning (HVAC) systems. The model accounts for pollutant-specific removal characteristics of the filters, mechanical airflow across filters, and ventilation of building or vehicle due to open windows or doors, and intake of outdoor air.

Time-Microenvironment Model

The time-microenvironment model is performed by the time-environment module 320 of the processing unit 24 and determines the time-spent in different indoor and outdoor microenvironments (e.g., home, work, school, in-vehicles) using a geocoded location 422 as described by:

(1) using, by way of example, the microenvironmental tracker (Micro Trac) model that is described in Breen et al. 2014, *GPS-based microenvironment tracker (Micro Trac) model to estimate time-location of individuals for air pollution assessments: Model evaluation in central North Carolina, Journal of Exposure Science and Environmental Epidemiology*, pages 412-420. Micro Trac uses building boundaries for each microenvironment (e.g., home, work) to distinguish between different microenvironments and to distinguish between indoors and outdoors.

(2) alternatively, by way of example, a time-microenvironment model completely different from MicroTrac, which does not use building boundaries, may be used. This time-microenvironment model:

a) automatically distinguishes between specific microenvironments that include home, work, school, based on a model that accounts for time-of-day and duration within closely spaced geo-location data, and from geo-coded building footprints available from public databases of satellite-based earth images 64.

b) automatically distinguishes between indoor and outdoor microenvironments based on unique data available from portable electronic devices, which includes: availability and strength of WiFi signal and cell tower signal, and distances between geolocation data based on a clustering algorithm.

Ventilation Model

The ventilation model 450 is performed by the ventilation module 330 and is described by:

(1) using accelerometer data (physical activity level 434) from the personal device 20, to classify physical activity level/intensity (sedentary, low, moderate, vigorous).

(2) using the output of the time-microenvironment model to determine time-spent inside vehicles, which is then used to prevent any misclassification while inside the vehicle (i.e., accelerometer detects motion of vehicle).

(3) estimating ventilation (L/min) based on activity intensity, age, gender, body weight from literature-reported tables (physical activity level/demographics 434).

(4) Calculating inhaled dose (g)=exposure (g/L)×ventilation (L/min)×sampling duration (min), which is output as dose 428 in FIG. 4. The exposure 426 is determined based upon the outputs from the indoor air quality model for home 410, the indoor air quality model for other microenvironments 424 and time-microenvironment model 430.

Alternatively, ventilation is determined from the personal wearable respiratory ventilation sensor 70.

Alternatively, by way of example, ventilation may be determined in a completely different way.

Personalized Risk Management Model

The personalized risk management model is performed by the personalized risk management module 340 of the processing unit 24.

The user input data (personal information) such as the user demographics 2.1, characteristics of the home of the user 2.2, operating conditions of the home 2.3, the user's home, work and school street addresses 2.4, and the health status of the user 2.5, and the personal health monitor data (personal condition data), such as the data from the personal wearable respiratory ventilation sensor 70 (which may comprise plethysmography chest bands), the personable wearable accelerometer sensor 72, the personal wearable heart rate sensor 74 and the personal wearable electrocardiogram sensor 76 are inputs into the personalized risk management model. In addition, the dose 428 is integrated with the health status 436, to generate the exposure and dose history 3.1, and the health status history 3.2, and to provide a notification 3.3 to the user 10 through the display unit 22 to modify his behavior. FIG. 4 shows input changes 480 (e.g., changes to user physical activity, user time-microenvironment, home operating conditions that include: indoor temperature settings, air cleaner settings, window fan settings, open windows) based on information (i.e., notifications) from a personalized risk management model 470. These input changes could be done manually by the user 10, or done automatically by communication (e.g., WiFi-enabled home thermostat to change home indoor temperature, WiFi-enabled home air cleaner to control settings.)

The modified inputs by the user 10 or the automated control system (e.g., WiFi-enabled home thermostat to change home indoor temperature, WiFi-enabled home air cleaner to control settings) 480 are fed back into the home building characteristics 412, the home window fan settings 414, the home open window status 416, the home indoor temperature settings 418, the home air cleaner settings 420, the geocoded location 432, and the physical activity level, demographics 434. The geocoded location 432 is fed back to the outdoor temperature, wind speed 422 and the time-micro environment model.

The application comprises an "integrated real-time feedback system" that uses the output (air pollution dose) to modify the inputs. This is then used to make "just-in-time" informed decisions to take action (e.g., notify a user to modify behavior related to air pollution, automated (via smartphone) operation of a home window, the home indoor temperature settings, the home air cleaner settings, to remove indoor sources of air pollution) to minimize adverse health effects. The functional aspects of the application are novel, not obvious, not well known, routine nor conventional.

The application has a "ventilation model" to predict inhaled dose from physical activity level, age, gender, body weight, and microenvironment. This ventilation model is novel, not obvious, not well known, routine nor conventional The application has a "personalized risk management model" that integrates health data with air pollution dose to determine dose that is likely to cause adverse health effects for a particular person's sensitivity to air pollution, and thus recommend actions to be taken (modify person's behavior as related to air pollution, automated operation of home-indoor air cleaner) to reduce dose and minimize adverse health effects. This personalized risk management model is novel, not obvious, not well known, routine nor conventional.

The application has an "indoor air quality model" that:
a. includes outdoor-generated air pollutants
b. includes indoor removal of air pollutants from operating home air cleaners
c. integrates with microenvironment model to determine dose when indoors at home.

This functional aspect is novel, not obvious, not well known, routine nor conventional. Other aspects and embodiments of the invention are novel, not obvious, not well known, routine nor conventional.

The application predicts "real-time" dose by a novel automated method of collecting the time-varying inputs via the internet and processing them with the models, and then displaying the results on a personal mobile device in real-time. The published models use a manually collected set of inputs and are used for specific field studies, retrospectively.

The application automatically collects inputs, runs models, and displays results on personal mobile devices (smartphones and other smart devices like smartwatches), and then iterates this process with continuously updated inputs. Therefore, the application can be used by the general public for reducing adverse health effects from air pollution. Published models, which require manual collection of inputs, specialized software to run the model, and display the results on non-mobile devices (i.e., laptops, desktops), are designed to be used only by highly-trained researchers in a post-processing mode.

The application has a "time-microenvironment model" that:

(1) automatically distinguishes between specific microenvironments that include home, work, school, based on novel model that accounts for time-of-day and duration within closely spaced geo-location data, and from geo-coded building types available from public databases.

(2) automatically distinguishes between indoor and outdoor microenvironments based on unique data available from portable electronic devices, which includes: availability and strength of WiFi signal and cell tower signal, distances between geo-location data based on a clustering algorithm.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A personal device of a user which receives geocoded outdoor air pollution, outdoor weather condition data from outdoor sensors, and satellite image data, and personal condition data from wearable sensors, the personal device comprising:
   a display unit to enable the user to enter personal information including home condition data and user characteristics;
   an accelerometer which detects a physical activity level of the user;
   a personal device locator which determines a location of the personal device; and
   a processing unit which determines building footprints from the satellite image data, determines a microenvironment location based upon the building footprints and the determined location, and uses the geocoded outdoor air pollution and outdoor wind speed and temperature data, the personal condition information, the physical activity level of the user, and the microenvironment to assess air pollution exposure and dose of the user;
   wherein:
   the personal device generates a notification to the user to modify behavior or at least one automated home condition that is controlled by the home condition data based upon the assessed air pollution exposure and dose of the user; and
   the processing unit uses the microenvironment and a time-micro-environment model to distinguish between at least two of the following microenvironments:
   outdoors, inside a home, inside a vehicle, inside a school, inside a workplace, or inside another type of building.

2. The personal device of claim 1, wherein the processing unit feeds back data on at least one of the modified user behavior or modified automated home condition to at least one home element controlled by the home condition data, location of user data, and physical activity level in making additional assessments of the air pollution exposure and dose of the user.

3. The personal device of claim 1, wherein:
   the personal information comprises at least one of:
   user demographics, home characteristics and operating conditions, user street address, and health status of the user;
   the geocoded outdoor air pollution and outdoor weather condition data comprises at least one of:
   geocoded outdoor air pollution;
   at least one of geocoded outdoor air temperature or geocoded outdoor wind speed; and
   satellite-based geocoded earth images.

4. The personal device of claim 3, wherein the personal device locator is a GPS sensor.

5. The personal device of claim 1, wherein the processing unit performs a ventilation model, wherein the ventilation model comprises:
   using the detected physical activity level from the accelerometer, to classify physical activity level intensity;
   using the time-microenvironment model to determine time spent outdoors, inside the school, inside the workplace, or inside another type of building;
   (3) estimating ventilation (L/min) based on the detected physical activity intensity and physical characteristics of the user; and
   determining inhaled dose (g)=exposure (g/L) x ventilation (L/min) x sampling duration (min), which is output;
   wherein the exposure is determined based upon at least one of indoor air quality for the home, indoor air quality for microenvironments other than the home and an amount of time of the personal device in each time-microenvironment model.

6. The personal device of claim 1, wherein the display unit generates the notification to the user visually.

7. The personal device of claim 6, wherein the processing unit performs a personalized risk management model, comprising:
   using the personal condition data and the exposure and the dose to provide the notification to the user to modify behavior;
   wherein the personal condition information comprises at least one of respiratory ventilation, acceleration, heart rate and electrocardiogram information from corresponding ones of the wearable sensors.

8. The personal device of claim 1, wherein the personal device generates a vibration or a sound as the notification to the user.

9. The personal device of claim 1, wherein:
   the personal device generates the notification to the user to modify the at least one home condition; and
   the home condition data comprises at least one of:
   home characteristics, including at least one of floor area, year built or number of stories; or
   home operating conditions, including at least one of window fan settings, open window status, indoor temperature settings, and air cleaner settings.

10. The personal device of claim 1, further comprising at least one of a:
    WiFi transmitter/receiver or cellular transmitter/receiver, wherein the processing unit automatically distinguishes between indoor and outdoor microenvironments based on at least one of:
    availability and strength of WiFi signal received by the WiFi transmitter/receiver or cell tower signal received by the cellular tower receiver; or
    distances between geolocation data based on a clustering algorithm.

11. A system to assess and manage air pollution exposure, comprising:
    the personal device of claim 1;
    the outdoor sensors;
    the wearable sensors; and a network to enable communication between the personal device, the outdoor sensors and the wearable sensors.

12. A method to assess and manage air pollution exposure and dose of a user, comprising:
receiving geocoded outdoor air pollution and outdoor weather condition data from outdoor sensors, and personal condition data from wearable sensors, on a personal device; enabling entry on the personal device of personal information including home condition data and user characteristics;
detecting a physical activity level of the user using acceleration of the personal device;
determining a location of the personal device;
determining building footprints from satellite image data, and determining a microenvironment based upon the building footprints and the determined location;
using the microenvironment and a time-micro-environment model to distinguish between at least two of the following microenvironments:
outdoors, inside a home, inside a vehicle, inside a school, inside a workplace, or inside another type of building;
using the geocoded outdoor air pollution and outdoor wind speed and temperature data, the personal condition information, the physical activity level of the user and the microenvironment to assess air pollution exposure and dose of the user; and
notifying the user to modify behavior or at least one automated home condition that is controlled by the home condition data based upon the assessed air pollution exposure and dose of the user.

13. The method of claim 1, further comprising:
feeding back data on at least one of the modified user behavior or modified automated home condition to at least one home element controlled by the home condition data, location of user data, and physical activity level in making additional assessments of the air pollution exposure and dose of the user.

14. The method of claim 1, wherein:
the personal information comprises at least one of:
user demographics, home characteristics and operating conditions, user street address, and health status of the user;
the geocoded outdoor air pollution and outdoor weather condition data comprises at least one of:
geocoded outdoor air pollution;
at least one of geocoded outdoor air temperature or geocoded outdoor wind speed; and
satellite-based geocoded earth images.

15. The method of claim 12, further comprising:
performing a ventilation model, wherein the ventilation model comprises:
using the detected physical activity level from the accelerometer, to classify physical activity level intensity;
using the time-microenvironment model to determine time spent outdoors, inside the school, inside the workplace, or inside another type of building;
estimating ventilation (L/min) based on the detected physical activity intensity and physical characteristics of the user; and
determining inhaled dose (g)=exposure (g/L) x ventilation (L/min) x sampling duration (min), which is output;
wherein the exposure is determined based upon at least one of indoor air quality for the home, indoor air quality for microenvironments other than the home and an amount of time of the personal device in each time-microenvironment model.

16. A non-transitory machine-readable medium storing a non-transitory, tangible computer program product comprising computer program code which when executed causes a processing unit in a personal device to perform the following operations comprising:
receiving geocoded outdoor air pollution and outdoor weather condition data from outdoor sensors, and personal condition data from wearable sensors;
receiving personal information including home condition data and user characteristics that have been entered to the personal device;
receiving a detected physical activity level of the user using acceleration of the personal device;
receiving a location from a locator of the personal device;
receiving satellite image data, determining building footprints from the satellite image data, and determining a microenvironment based upon the building footprints and the location;
using the microenvironment and a time-micro-environment model to distinguish between at least two of the following microenvironments:
outdoors, inside a home, inside a vehicle, inside a school, inside a workplace, or inside another type of building;
using the geocoded outdoor air pollution and outdoor wind speed and temperature data, the personal condition information, the physical activity level of the user and the microenvironment to assess air pollution exposure and dose of the user; and
generating a notification for the user to modify behavior or at least one automated home condition that is controlled by the home condition data based upon the assessed air pollution exposure and dose of the user.

17. The non-transitory machine-readable medium of claim 16, wherein the processing unit generates feed back data on at least one of the modified user behavior or modified automated home condition to at least one home element controlled by the home condition data, location of user data, and physical activity level in making additional assessments of the air pollution exposure and dose of the user.

* * * * *